US012558139B2

(12) United States Patent
Ma et al.

(10) Patent No.: US 12,558,139 B2
(45) Date of Patent: Feb. 24, 2026

(54) MANAGING DELIVERY OF REFRIGERANTS TO MEDICAL DEVICES

(71) Applicant: Medtronic, Inc., Minneapolis, MN (US)

(72) Inventors: Wing-Choi Ma, Maple Grove, MN (US); Nicholas Ruchti, Minneapolis, MN (US); Nicholas L. Nagel, Blaine, MN (US); Martin Rochon, Les Cedres (CA); Daniel T. Dreier, Mounds View, MN (US); Cary M. Ley, Plymouth, MN (US); Julia A. Schraut, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 18/159,212

(22) Filed: Jan. 25, 2023

(65) Prior Publication Data

US 2023/0233243 A1 Jul. 27, 2023

Related U.S. Application Data

(60) Provisional application No. 63/303,215, filed on Jan. 26, 2022.

(51) Int. Cl.
*A61B 18/02* (2006.01)
*A61B 18/00* (2006.01)

(52) U.S. Cl.
CPC .... *A61B 18/02* (2013.01); *A61B 2018/00666* (2013.01); *A61B 2018/0072* (2013.01);
(Continued)

(58) Field of Classification Search
CPC .......... A61B 18/02; A61B 2018/00666; A61B 2018/00714; A61B 2018/0212; A61B 2018/0262
See application file for complete search history.

(56) References Cited

U.S. PATENT DOCUMENTS 5,209,126 A 5/1993 Grahn
5,364,392 A * 11/1994 Warner .............. A61B 18/1815
607/101

(Continued)

FOREIGN PATENT DOCUMENTS

CN 109431594 A 3/2019
EP 3228272 A1 10/2017
WO 2018130096 A1 7/2018

OTHER PUBLICATIONS

Holt, "Back to Basics—Overcurrent Protection—Incomplete", Mike Holt Enterprises, Inc., 2021, 1 page.
(Continued)

*Primary Examiner* — Daniel W Fowler
(74) *Attorney, Agent, or Firm* — Michael Best & Friedrich LLP

(57) ABSTRACT

Systems and methods for controllable delivery of pressurized refrigerant to a medical device, such as a cryoablation catheter. In some examples, a delivery system includes a tank holding the pressurized refrigerant, an electrical heater arranged to heat the tank, and an electronic controller connected to regulate the heater based on input signals received from a plurality of sensors including a temperature sensor in thermal contact with the exterior surface of the tank and a pressure sensor for measuring pressure in the refrigerant-delivery line connecting the tank to the medical device. In operation, the electronic controller processes the input signals by comparing values of at least some of the input signals with respective threshold values and uses logic operations configured for combined processing of two or more of the input signals to decide when to switch the heater between an ON state and an OFF state.

18 Claims, 4 Drawing Sheets

(52) U.S. Cl.
CPC ............... *A61B 2018/00797* (2013.01); *A61B 2018/00821* (2013.01); *A61B 2018/0212* (2013.01)

(56) References Cited

U.S. PATENT DOCUMENTS

| | | | |
|---|---|---|---|
| 2002/0058933 A1* | 5/2002 | Christopherson ...... | A61B 18/14 |
| | | | 606/41 |
| 2007/0277550 A1 | 12/2007 | Li et al. | |
| 2009/0270954 A1* | 10/2009 | Schenck ............... | A61B 18/14 |
| | | | 607/102 |
| 2015/0300569 A1* | 10/2015 | Baust ........................ | F17C 5/02 |
| | | | 62/50.1 |
| 2016/0022345 A1 | 1/2016 | Baust et al. | |
| 2016/0120585 A1* | 5/2016 | Poulsen ................. | A61B 18/04 |
| | | | 606/31 |
| 2016/0220294 A1 | 8/2016 | Babkin et al. | |
| 2019/0000524 A1* | 1/2019 | Rosen ................... | A61F 7/0085 |
| 2019/0247105 A1* | 8/2019 | Harmouche .............. | G01F 9/00 |
| 2019/0262061 A1* | 8/2019 | Cheng ................ | A61B 18/1402 |
| 2020/0022745 A1* | 1/2020 | McHale .................. | A61B 18/02 |
| 2021/0000521 A1* | 1/2021 | Tearney .................. | A61B 10/04 |
| 2021/0161577 A1 | 6/2021 | Johansson | |
| 2021/0228254 A1* | 7/2021 | Mayer .................... | A61B 18/02 |
| 2023/0248411 A1* | 8/2023 | Fox ........................ | A61B 90/37 |
| | | | 606/21 |

OTHER PUBLICATIONS

Burke et al., "Tactile Robotic Topographical Mapping Without Force or Contact Sensors", Apr. 2008, NASA's Jet Propulsion Laboratory, Mechanical & Fluid Systems, <Thttps://www.techbriefs.com/component/content/article/tb/pub/briefs/mechanics-and-machinery/2702>.

Roth et al., "An Improved Tibial Force Sensor to Compute Contact Forces and Contact Locations In Vitro After Total Knee Arthroplasty", J Biomech Eng., 2017, vol. 139, No. 4, 36 pages.

Pandya et al., "MEMS-Based Flexible Force Sensor for Tri-Axial Catheter Contact Force Measurement", J. Microelectromech Syst., 2017, vol. 26, No. 1, pp. 264-272.

Watanabe et al., "Development of a measuring system of contact force during braille reading using an optical 6-axis force sensor", Conf Proc IEEE Eng Med Biol Soc., 2006, pp. 4936-4940.

Ferre et al., "Design of a lightweight, cost effective thimble-like sensor for haptic applications based on contact force sensors", Sensors, 2011, vol. 11, No. 12, pp. 11495-509.

Maeda et al., "A MEMS hardness sensor with reduced contact force dependence based on the reference plane concept aimed for medical applications", Japanese Journal of Applied Physics, 2016, vol. 55, Issue 4S, pp. 04EF11.

Nidek et al., "Heating Elements", TUTCO Heating Solutions Group, 2021, <https://farnam-custom.com/heating-elements>, 10 pages.

DMQ, "Refrigerant Flow Controls Technology", 2021, <https://www.dmq-us.com/refrigerant-flow-control-technology/>, 2 pages.

Instrumart, "Temperature Controller Basics Handbook", 2021, <https://www.instrumart.com/pages/283/temperature-controller-basics-handbook>, 9 pages.

Schaefer, "What Is a Thermocouple? the defintion:", Industrial Heating Systems, 2021, <https://industrialheatingsystems.com/Whatis-thermocouple.html>, 4 pages.

European Patent Office Extended Search Report for Application No. 23150153.7 dated Jun. 23, 2023 (10 pages).

Cuesta et al., "Sensor Prototype to Evaluate the Contact Force in Measuring with Coordinate Measuring Arms", PubMed Central, 2015, pp. 13242-13257.

European Patent Office Exam Report for Application No. 23 150 153.7 dated Aug. 11, 2025 (6 pages).

* cited by examiner

MANAGING DELIVERY OF REFRIGERANTS TO MEDICAL DEVICES

CROSS-REFERENCE TO RELATED APPLICATIONS

This application claims the benefit of U.S. Provisional Patent Application No. 63/303,215, filed 26 Jan. 2022, and entitled "METHOD FOR MANAGING REFRIGERANT PRESSURE FOR CRYOABLATION AND CRYOMAPPING."

FIELD

This application relates generally to methods and apparatus for managing delivery of refrigerants to medical devices, and more particularly but not exclusively, to cryoablation and cryomapping.

BACKGROUND

Cryoablation is a process that uses extreme cold to destroy tissue. In various examples, cryoablation is performed using a hollow conduit (e.g., a cryoprobe) through which a cooled, thermally conductive fluid is circulated. The cryoprobe is positioned adjacent to the target area in the body in such a way that the delivered cold destroys the diseased tissue.

Cryomapping is typically used complementarily to cryoablation. In an example application, cryomapping is performed to confirm target sites for cryoablation. When the cell temperatures do not fall below a certain (low) temperature, the cold-induced physiological changes are mostly reversible, and the cells recover their precooling function when warmed. In the electrophysiology laboratory, temporary changes induced by the cryoprobe during cryomapping are detected and evaluated to judge the efficacy and/or safety of the prospective cryoablation.

SUMMARY

Disclosed herein are, among other things, various examples, aspects, features, and embodiments of systems and methods for controllable delivery of pressurized refrigerant to a medical device, such as a cryoablation catheter. In some examples, a delivery system includes a tank holding the pressurized refrigerant, an electrical heater arranged to heat the tank, and an electronic controller connected to regulate the heater based on input signals received from a plurality of sensors including a temperature sensor in thermal contact with the exterior surface of the tank and a pressure sensor for measuring pressure in the refrigerant-delivery line connecting the tank to the medical device. In operation, the electronic controller processes the input signals by comparing values of at least some of the input signals with respective threshold values and uses logic operations configured for combined processing of two or more of the input signals to decide when to switch the heater between an ON state and an OFF state.

One example provides a system for delivering a refrigerant to a medical device. The system includes a confined volume to hold pressurized refrigerant therein and an electrical heater arranged to heat the confined volume. The system also includes an electronic controller connected to regulate the heater based on input signals received from a plurality of sensors including a temperature sensor in thermal contact with the confined volume and a pressure sensor for measuring a pressure in a refrigerant-delivery line connecting the confined volume and the medical device.

Another example provides a method for delivering a refrigerant to a medical device. The method includes driving an electrical current, with a power supply, through an electrical heater arranged to heat a confined volume holding pressurized refrigerant therein. The method also includes regulating the electrical current with an electronic controller connected to the power supply, the regulating being based on input signals received by the electronic controller from a plurality of sensors including a temperature sensor in thermal contact with the confined volume and a pressure sensor for measuring a pressure in a refrigerant-delivery line connecting the confined volume and the medical device.

BRIEF DESCRIPTION OF THE DRAWINGS

Some embodiments will be better understood by reference to the following detailed description when considered in conjunction with the accompanying drawings wherein.

DETAILED DESCRIPTION

Figure 1:
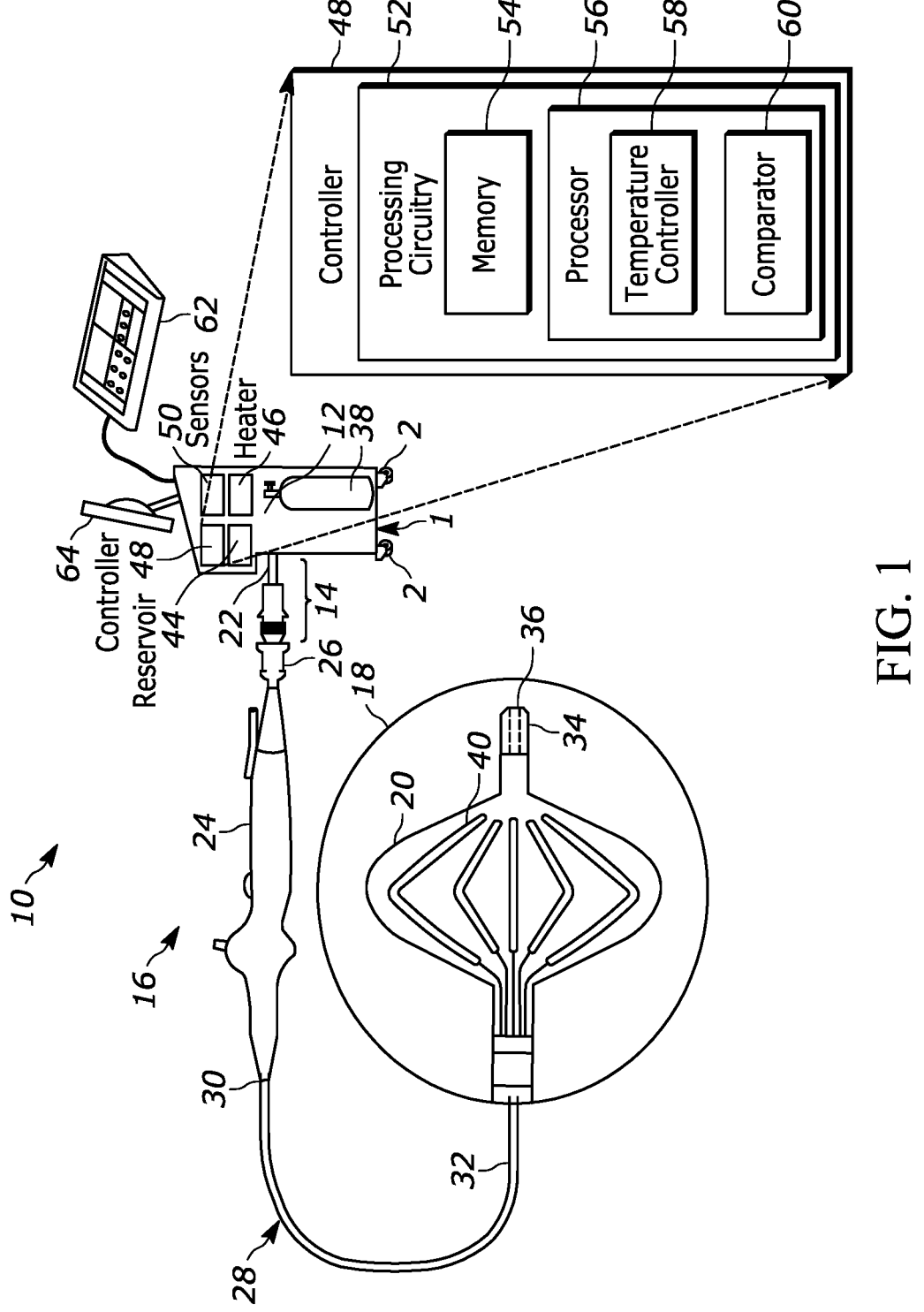
FIG. 1 is a schematic diagram illustrating a medical system according to various examples.

Catheter cryoablation is a technique that has applications in, for example, cancer, nerve, and cardiac treatment. In some examples, cryoablation is used to control heart rhythm by ablating certain tissues that cause abnormal heart rhythms. A cryoablation catheter is used to create lesions at locations where heat is rapidly removed thereby from cardiac cells by delivery of pressurized refrigerant, such as nitrous oxide ($N_2O$), with a controlled mass flow rate. Heat is transferred when the pressurized refrigerant expands and evaporates at the catheter tip. Cardiac cell lesions are created by the rapid removal of heat from the tissue.

Catheter cryomapping is a focal catheter technique used to reversibly impair an action potential of cardiac cells without creating lesions. One purpose of this technique is to identify the effectiveness of potential locations for cryoablation prior to creating a lesion. Cryomapping is similar to cryoablation in that the catheter is placed at the target site where heat is rapidly removed from cardiac cells by the refrigerant. Cryomapping differs from cryoablation in that cryomapping is typically controlled through monitoring the catheter tip temperature and adjusting the flow of the refrigerant to maintain that temperature at a higher target value.

A console is provided to control the delivery of pressurized refrigerant. During cryomapping, the console is used to monitor the cryoablation catheter's temperature and control the delivery of the pressurized refrigerant to the tip of the cryoablation catheter, such as a focal catheter, to maintain a target temperature. Clinically, the temperature during cryomapping is set so that the effect the refrigerant has on the cardiac cell tissue is reversible. The console has a tank configured to hold the pressurized refrigerant. The pressure of the delivered refrigerant is affected by the temperature and pressure of the refrigerant in the tank.

The pressure versus temperature relationship is governed by thermodynamic principles. In a typical example, the refrigerant is held under relatively high pressure (e.g., 760 PSIG) to remain in liquid form until the refrigerant reaches the tip of the cryoablation catheter, where a pressure change occurs, from the high pressure to approximately atmospheric pressure, leading to a phase change from liquid to vapor. This thermodynamic process absorbs heat from the tissues surrounding the catheter tip and causes cryoablation of some of the tissues. In a cold room environment or with a cold pressurized refrigerant source, the pressure of the refrigerant may not be high enough to perform optimal cryotherapy.

In general, depending on the ambient conditions around the console and/or tank, the pressure of the refrigerant may be low or high. When the pressure of the refrigerant is low, it typically takes a relatively long time to bring the pressure of the refrigerant up to a desired level, leading to potential inconsistencies in therapeutic procedures. Low refrigerant pressure also increases the risk of malfunction within the console, which manifests itself as inability to meet a target mass flow rate for cryoablation or inability to maintain a target catheter-tip temperature for cryomapping.

At least some of the above-indicated problems in the state of the art can beneficially be addressed using various methods and systems for managing refrigerant pressure disclosed herein. For example, in a cold environment, or with a tank of pressurized refrigerant stored in a cold environment, the pressure of the refrigerant in the tank may not be high enough to deliver optimal cryotherapy, and a long warmup time is needed for the pressure to rise to a needed level. Some embodiments overcome the latency of bringing the pressurized refrigerant up to a desired pressure by providing a heating element removably affixed to at least one of a reservoir and/or a tank that serves as a source of pressurized refrigerant for a cryoablation catheter. The reservoir and/or tank has/have pressurized refrigerant therein. In some embodiments, there is a tank but no reservoir. In some embodiments, there is a reservoir only, the reservoir being fed by an external high-pressure refrigerant line. In some embodiments, there are both a tank and a reservoir, and either one or both may be heated. In some examples, the reservoir is smaller than the tank and can be heated more quickly and efficiently than the tank. An electronic controller is provided to control the delivery of pressurized refrigerant based at least in part on a detected pressure and/or a detected temperature at various points in the system. In some embodiments, a pressure control loop is provided to drive a difference between a target pressure and an estimated or measured pressure toward zero.

Before describing in detail various example embodiments, it should be noted that some embodiments reside primarily in combinations of apparatus components and processing steps related to control systems or circuits. Accordingly, components have been represented where appropriate by conventional symbols in the drawings, showing only those specific details that are pertinent to understanding the embodiments so as not to obscure the disclosure with details that will be readily apparent to those of ordinary skill in the pertinent art having the benefit of the description herein. Like numbers refer to like elements throughout the description.

It should be understood that various aspects disclosed herein may be combined in different combinations than the combinations explicitly presented in the description and accompanying drawings. It should also be understood that, depending on the example, certain acts or events of any of the processes or methods described herein may be performed in a different sequence, may be added, merged, or left out altogether (e.g., all described acts and/or events may not be necessary to carry out some of the techniques). In addition, while certain aspects of this disclosure are described as being performed by a single module or unit for purposes of clarity, it should be understood that the techniques of this disclosure may be performed by a combination of units or modules associated with, for example, a medical device.

FIG. 1 is a schematic diagram illustrating a medical system 10 according to various examples. The system 10 can be used for various cryotherapy procedures, including cryo-mapping and cryoablation, in different respective operating modes thereof. In the example shown, the system 10 includes a console 12 coupled to an umbilical system 14. The console 12 has wheels 2 attached to a base plate 1 thereof and, as such, is wheelable to different convenient locations in the treatment room. The umbilical system 14 is further coupled to a cryoablation catheter 16. In some examples, the cryoablation catheter 16 includes a suitable treatment device, such as a treatment device with a treatment portion 18 including an inflatable portion 20. In some other examples, the cryoablation catheter 16 does not have the inflatable portion 20 and/or has a different type of the treatment portion 18, e.g., corresponding to a focal catheter design.

The umbilical system 14 includes a coaxial cable umbilical 22 connected to the console 12 at one end thereof and to the cryoablation catheter 16 at the opposite end thereof. The coaxial cable umbilical 22 includes a cooling injection umbilical and a vacuum umbilical that provide respective inlet and return paths for the pressurized refrigerant used to cool a tissue-treating end of the treatment portion 18. The cooling injection umbilical is used to transfer the pressurized refrigerant from the cryoablation console 12 to the cryoablation catheter 16. The vacuum umbilical is used to allow the refrigerant, in liquid or gaseous state, to escape from the cryoablation catheter 16 back to the cryoablation console 12.

The cryoablation catheter 16 includes a handle 24 having a coaxial connector 26 with both an injection lumen and a vacuum lumen therein. The cryoablation catheter 16 further includes an elongated body 28 providing flow paths for the refrigerant between a proximal portion 30 and a distal portion 32 thereof. The distal portion 32 is connected to a distal end 34 of the cryoablation catheter 16. The distal end 34 includes a thermal tip 36 with a lumen therein. The elongated body 28 is typically flexible to allow insertion into and passage through a natural orifice. In operation, cold pressurized refrigerant is injected into the cooling injection umbilical within the elongated body 28 and delivered to the treatment portion 18 of the cryoablation catheter 16. The vacuum umbilical within the elongated body 28 evacuates the refrigerant from the treatment portion 18 back to the cryoablation console 12. In various examples, the treatment portion 18 has no electrodes or at least one electrode 40 configured to contact adjacent tissue and sense electrical activity thereat. It will be understood that the at least one electrode 40 represents one or more electrodes in a variety of different shapes, sizes, and configurations.

In various examples, the cryoablation catheter 16 is coupled, via the coaxial cable umbilical 22, to a tank 38 located in the console 12 or indirectly to an external high-pressure line connected to the console 12 to supply pressurized refrigerant. When the external high-pressure line provides the pressurized refrigerant, rather than the tank 38, the external high-pressure line is typically connected directly to a reservoir 44, which is configured to receive the pressurized refrigerant therefrom and then dispense the refrigerant, via the coaxial cable umbilical 22, to the cryoablation catheter 16. Either the tank 38 or the reservoir 44 is heated according to some examples described herein. In some examples, the tank 38 is coupled to the reservoir 44, which is further coupled to the cryoablation catheter 16. Thus, in some examples, the console 12 has the tank 38 but no reservoir 44, in which case the tank 38 is heated. In some other examples, the console 12 has the reservoir 44 but no tank 38, in which case the reservoir 44 is heated. In yet some additional examples, the console 12 has both the tank 38 and the reservoir 44. In such additional examples, one or both of the tank 38 and the reservoir 44 are heated. Typically, the tank 38 is used as a standalone source of pressurized refrigerant, whereas the reservoir 44 is used as a holding volume that receives pressurized refrigerant from another source, such as the tank 38 or the external high-pressure line.

The system 10 includes one or more heaters 46 thermally coupled, directly or indirectly, to the tank 38 and/or the reservoir 44 and configured to heat the pressurized refrigerant in at least one of the reservoir 44 and the tank 38. A temperature increase caused by the heating typically results in a corresponding increase in the pressure of the pressurized refrigerant, e.g., to a level sufficient for efficient delivery of the pressurized refrigerant to the distal end 34 of the cryoablation catheter 16. In some examples, the reservoir 44 is smaller than the tank 38, which enables more rapid heating of the deliverable pressurized refrigerant therein than when the heating is applied to the tank 38 but not to the reservoir 44 or when the reservoir 44 is absent.

The console 12 also includes an electronic controller 48 in communication with various system elements associated with the tank 38 and/or reservoir 44, including, inter alia, the one or more heaters 46. For example, the electronic controller 48 is typically in communication with one or more sensors 50 variously placed in or near the console 12. In various examples, the one or more sensors 50 include a thermocouple configured to sense a temperature of the tank 38 or the reservoir 44 and/or a pressure transducer configured to sense a pressure of the pressurized refrigerant at an output port of the tank 38 or the reservoir 44 or along the refrigerant-delivery plumbing. In some examples, multiple reservoirs 44 are implemented, with each of such reservoirs being outfitted with a respective one of the heaters 46 for faster temperature increase, which typically results in a corresponding faster pressure increase for the deliverable pressurized refrigerant.

In at least some examples, the heater(s) 46 is (are) connected to an electrical circuit configured to provide overcurrent protection, such as protection by an electrical fuse or other suitable circuit breaker. The heaters 46 are also typically provided with suitable thermal and electrical insulation and with mechanical fasteners to be removably affixed or strapped to the tank 38 and/or to the reservoir 44 so that good thermal contact is achieved thereby. In some additional examples, instead of being removably attached to the tank 38 or the reservoir 44, a heater 46 is fixedly attached thereto, e.g., by being a part of the body or structure defining the corresponding confined volume.

In some examples, the electronic controller 48 controls the amount of heat provided by the heater(s) 46 by intermittently turning the heater(s) 46 ON and OFF, e.g., based on the applicable control algorithm or logic and in response to streams of measurements provided by the sensors 50. In some other examples, the electronic controller 48 operates to continuously and gradually adjust the electrical currents flowing through the heater(s) 46 in response to the streams of measurements provided by the sensors 50. In various examples, the electronic controller 48 also operates to limit the temperature of or the amount of heat provided by the heater(s) 46 to avoid any heat-induced damage to the tank 38, the reservoir 44, and/or other heat-sensitive components of the console 12. In some examples, the electronic controller 48 is programmed to turn OFF the heater(s) 46 when a door to the portion of the console 12 enclosing the tank 38 and/or reservoir 44 is unlocked or open.

The electronic controller 48 includes processing circuitry 52 configured to operate and control the various functions of the console 12 and of the cryoablation catheter 16. The cryoablation catheter 16 is typically configured for diagnostic, energetic, therapeutic, and/or investigatory interactions with a treatment site. During at least some of such interactions, the system 10 operates to deliver adequate quantities of the pressurized refrigerant to the inflatable portion 20 and/or the thermal tip 36 of the cryoablation catheter 16.

In the example shown, the processing circuitry 52 includes a memory 54 and a processor 56. The processor 56 is configured to access (e.g., write to and/or read from) the memory 54. The processor 56 includes an electronic temperature controller 58 and a comparator 60, among other circuits. In operation, the processing circuitry 52 controls, executes, and/or supports various functions, methods, and/or processes described herein. The memory 54 is configured to store data, programmatic software code, and/or other pertinent information described herein. Some pieces of the software include instructions that, when executed by the processor 56 and/or processing circuitry 52, cause the system 10 to perform various operations and processes described herein.

In various examples, various circuits of the electronic controller 48 are in communication with a user interface device 62 that enables an operator to operate the system 10 and input values of various control parameters, such as a target pressure for the delivery of pressurized refrigerant to the cryoablation catheter 16. In some examples, the user interface device 62 includes a keyboard and a mouse. A display device 64 connected to the electronic controller 48 is typically used to display various system parameters, such as temperatures and pressures at various location in the system 10, e.g., the temperatures in and near the confined volumes 38, 44 and the pressure of the refrigerant along the delivery line. The display device 64 is also typically used to display various indicators, e.g., an indicator of whether a particular heater 46 is ON or OFF.

When pressurized refrigerant is injected into the treatment portion 18 via the elongated body 28, the inflatable portion 20 expands, causing the electrodes 40 to contact surrounding tissue and sense electrical activity in the tissue in the vicinity of the electrodes 40. The electrical signals sensed by the electrodes 40 are conducted by wires to the electronic controller 48, wherein the electrical signals are recorded in the memory 54. The sensed electrical signals may also be optionally displayed on the display device 64.

In addition to or in the alternative to the inflatable portion 20, the thermal tip 36 is used to remove heat from the adjacent tissue to reach a first temperature for cryomapping and to reach a second temperature for cryoablation. The target temperature for the thermal tip 36 is higher for cryomapping than for cryoablation, as indicated above.

In some examples, the tank 38 is the source of the pressurized refrigerant within the console 12. In various examples, the refrigerant is $N_2O$ or another type of cooling gas, fluid, and/or liquid. The console 12 typically has internal piping or plumbing through which the refrigerant can be transferred from the tank 38 to the reservoir 44, before being transferred to the cryoablation catheter 16 via the coaxial cable umbilical 22. At the distal end of the coaxial cable umbilical 22, inside the cryoablation catheter 16, the pressurized refrigerant is released inside the catheter tip cavity, which is typically held under a relatively low pressure, e.g., some degree of vacuum. Both the phase change from liquid to gas and sudden expansion of the pressurized refrigerant are endothermic processes, which cause a temperature drop resulting in the catheter tip 36 and/or the inflatable portion 20 cooling down, in some cases to below freezing. The refrigerant vapor is returned from the cryoablation catheter 16 through the vacuum path of the umbilical system 14 back to the console 12, where the vapor is evacuated and/or exhausted.

In some examples, the electronic temperature controller 58 operates to set a temperature of the pressurized refrigerant in the reservoir 44 and/or the tank 38 via the one or more heaters 46. The sensors 50 include variously located temperature sensors, e.g., thermocouples. The comparator 60 receives temperature measurements from the temperature sensors 50 and compares the measured temperatures with one or more target temperatures set for the corresponding locations by the temperature controller 58. Based on the comparison, the electronic temperature controller 58 operates the one or more heaters 46 to reach and maintain the target temperatures at those locations. In various examples, the values of the target temperatures are provided to the electronic temperature controller 58 by the operator via the input device 62 or by the applicable control algorithm run by the processing circuit 52.

Figure 2:
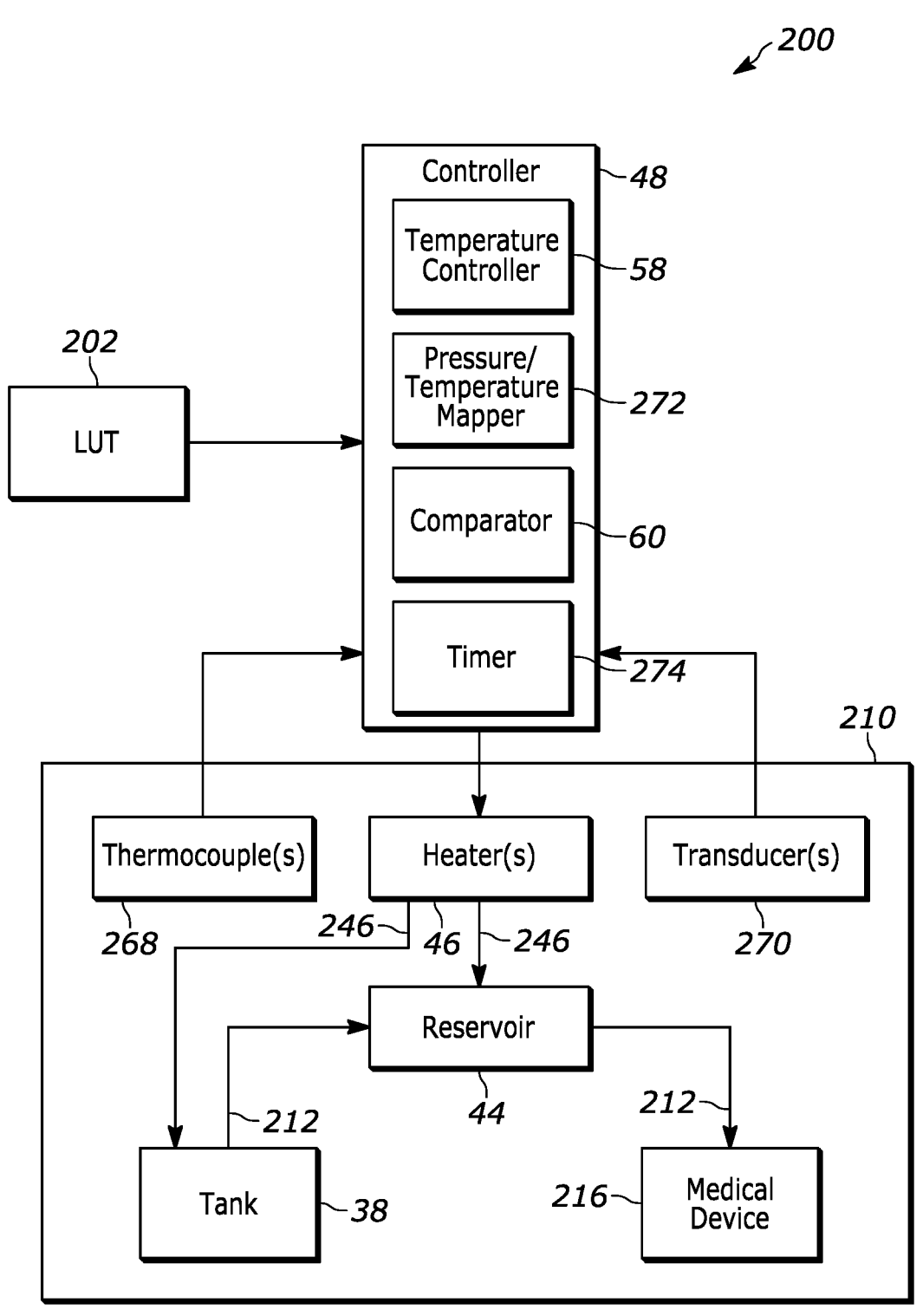
FIG. 2 is a block diagram illustrating an electrical circuit used in the medical system of FIG. 1 according to various examples.

FIG. 2 is a block diagram illustrating an electrical circuit 200 used in the system 10 according to various examples. The electrical circuit 200 is operatively coupled to a refrigerant delivery sub-system 210 of the system 10 as indicated in FIG. 2. In the example shown, the sub-system 210 includes the tank 38 and the reservoir 44 serially connected by piping 212 to a medical device 216. In some examples, the medical device 216 is or comprises the cryoablation catheter 16. In some other examples, the medical device 216 is another medical device configured to use pressurized refrigerant for its operation. The electrical circuit 200 comprises the electronic controller 48, one or more thermocouples 268, the one or more heaters 46, and one or more pressure transducers 270. The thermocouple(s) 268 and the pressure transducer(s) 270 are examples of the sensors 50 (FIG. 1).

In some examples, the electrical circuit 200 receives an input from a lookup table (LUT) 202 having stored therein calibration data and/or various configuration parameters corresponding to different ones of the medical devices 216. In various examples, the medical devices 216 differ by type, model, and/or manufacturer. The electronic controller 48 is configured to automatically recognize different medical devices 216 and access the LUT 202 to retrieve therefrom the calibration data and pertinent configuration parameters corresponding to the specific medical device 216 presently connected to the refrigerant delivery sub-system 210, as recognized by the electronic controller 48. The electronic controller 48 is further configured to use the retrieved calibration data and configuration parameters to operate the electrical circuit 200 to ensure optimal delivery of pressurized refrigerant to that specific medical device 216. In various examples, the LUT is stored in an external non-transient memory or in the memory 54.

In the example shown, in addition to the temperature controller 58 and the comparator 60 described above, the controller 48 includes a pressure/temperature mapper 272 configured to map a target pressure to a target temperature. In some examples, the pressure/temperature mapper 272 is also configured to estimate a reservoir temperature by mapping the pressure measured by the pressure transducer 270 to a reservoir temperature. In some other examples, the reservoir temperature is directly monitored using the corresponding one of the thermocouples 268. The comparator 60 is configured to determine a difference between the target temperature and the measured or estimated reservoir temperature to produce a temperature error signal. The electronic controller 48 is configured to regulate heat flows 246 generated by the corresponding heaters 46 based on the temperature error signal, e.g., to drive the temperature error signal toward zero.

In some additional examples, the comparator 60 is configured to determine a difference between the target pressure and the pressure measured by the corresponding one of the pressure transducers 270 to determine a pressure error. The pressure/temperature mapper 272 operates to map the determined pressure error to a new temperature setting. The temperature controller 58 then uses this new temperature setting to set a heat output of the heater(s) 46 to achieve the target pressure. In some examples, the temperature controller 58 is also responsive to measurements of the environmental or ambient temperature inside and/or outside the console 12, based on which the electronic controller 48 further regulates the heater(s) 46.

In some examples, the console 12 supports a graphical user interface (GUI), e.g., using the input device 62 and the display device 64, which enable an operator of the console 12 to set the target pressure(s) and temperature(s). For some procedures, the electronic controller 48 is configured to cycle through a sequence of temperature/pressure settings based at least in part on a plurality of target settings entered through the GUI. An example sequence of settings typically corresponds to successive time intervals. A timer 274 included with the electronic controller 48 is used to appropriately clock the time intervals and/or to limit a time duration of an ON state of selected heaters 46.

Figure 3:
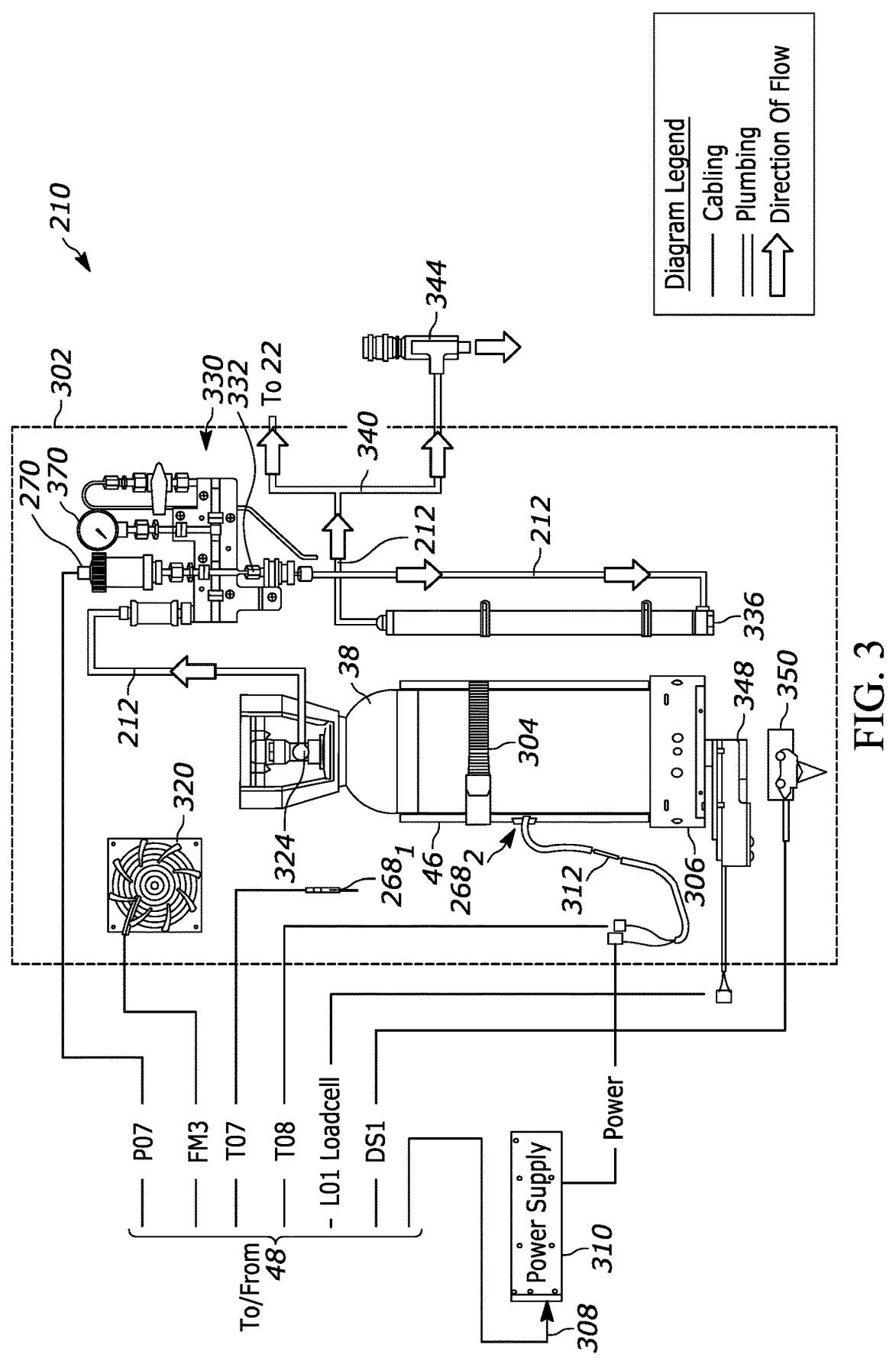
FIG. 3 is a schematic diagram illustrating a refrigerant delivery sub-system of the medical system of FIG. 1 according to various examples.

FIG. 3 is a schematic diagram illustrating the refrigerant delivery sub-system 210 of the system 10 according to various examples. In the example shown, the sub-system 210 includes a cabinet-type enclosure 302, wherein the tank 38 is located. The reservoir 44 is absent. In at least some examples, the enclosure 302 is a part of the console 12 and has an access door, which can be closed and locked to secure the interior space of the enclosure, e.g., against accidental or unauthorized entry. A door sensor 350 is connected, via a wireline DS1, to the electronic controller 48 to indicate thereto the door status, which can be, e.g., open or closed.

In the example shown, the heater 46 is a blanket-type heater that is wrapped around the bottle-shaped tank 38 and strapped thereto using an adjustable strap or belt 304. In various examples, the blanket-type heater 46 covers between 30% and 60% of the lateral surface area of the bottle-shaped tank 38. The bottom of the bottle-shaped tank 38 is secured in a cylindrically shaped receptacle 306 equipped with a weight monitor (e.g., digital scale) 348. The weight monitor 348 is connected, via a wireline L01 LOADCELL, to the electronic controller 48 to provide a reading of the present weight load in the receptacle 306. When the bottle-shaped tank 38 is in the receptacle 306, the weight load is the weight of the tank. In operation, the weight of the bottle-shaped tank 38 changes due to the refrigerant consumption. When the bottle-shaped tank 38 is not in the receptacle 306, the weight load is zero.

A power supply 310 is connected, via a power line POWER, to the blanket-type heater 46 to drive therethrough a controllable electrical current. In operation, the power supply 310 sets the magnitude of this current in response to a control signal 308 received from the electronic controller 48. In some examples, the control signal 308 causes the power supply 310 to toggle the magnitude of the current between zero (OFF state, no current) and a fixed value (ON state). An overcurrent fuse 312 protects the blanket-type heater 46 from sudden (e.g., accidental) surges of the electrical current driven therethrough by the power supply 310.

A thermocouple 2681 is configured to measure the air temperature within the enclosure 302. The thermocouple 2681 is connected, via a wireline T07, to the electronic controller 48 to provide readings of the air temperature thereto. In response to the temperature readings received from the thermocouple 2681, the electronic controller 48 operates to regulate, via a control wireline FM3, the rotation speed of a fan 320. In various examples, the fan 320 is used to circulate the air within the enclosure 302 and/or to provide intake of external ambient air into the enclosure 302 for ventilation and thermal management.

A thermocouple 2682 is integrated into or attached to the blanket-type heater 46 to monitor the surface temperature of the bottle-shaped tank 38. The thermocouple 2682 is connected, via a wireline T08, to the electronic controller 48 to provide readings of the tank's surface temperature thereto. The electronic controller 48 is configured to use the temperature readings received from the thermocouple 2682 as one of the inputs for the pertinent algorithm or decision block directed at generating the control signal 308 for the power supply 310.

An output port 324 of the bottle-shaped tank 38 is connected, via a first section of the piping 212, to a manifold 330 having connected thereto, inter alia, the electronic pressure gauge (pressure transducer) 270 and a mechanical pressure gauge 370. The electronic pressure gauge 270 is connected, via a wireline P07, to the electronic controller 48 to provide readings of the refrigerant pressure thereto. The electronic controller 48 is configured to use the pressure readings received from the electronic pressure gauge 270 as one of the inputs for the pertinent algorithm or decision block directed at generating the control signal 308 for the power supply 310. The mechanical pressure gauge 370 is typically used for visual indication of the refrigerant pressure in the manifold 330.

A second section of the piping 212 connects a port 332 of the manifold 330 to an input port of a desiccant filter 336. A third section of the piping 212 connects an output port of the filter 336 to an input of a T-shaped line splitter 340. The two outputs of the T-shaped line splitter 340 are connected to the coaxial cable umbilical 22 (also see FIG. 1) and a pressure relief valve 344, respectively. In some examples, the connection from the splitter 340 to the coaxial cable umbilical 22 is indirect and runs through one or more additional components, such as such as a flow meter, etc. The filter 336 operates to remove moisture (i.e., water, in liquid and/or gaseous form) from the refrigerant flowing therethrough. The pressure relief valve 344 operates to vent the excess refrigerant from the piping 212 when the refrigerant pressure exceeds a certain threshold pressure, e.g., 1100 PSI. In some examples, the pressure relief valve 344 is replaced by a different suitable element.

Figure 4:
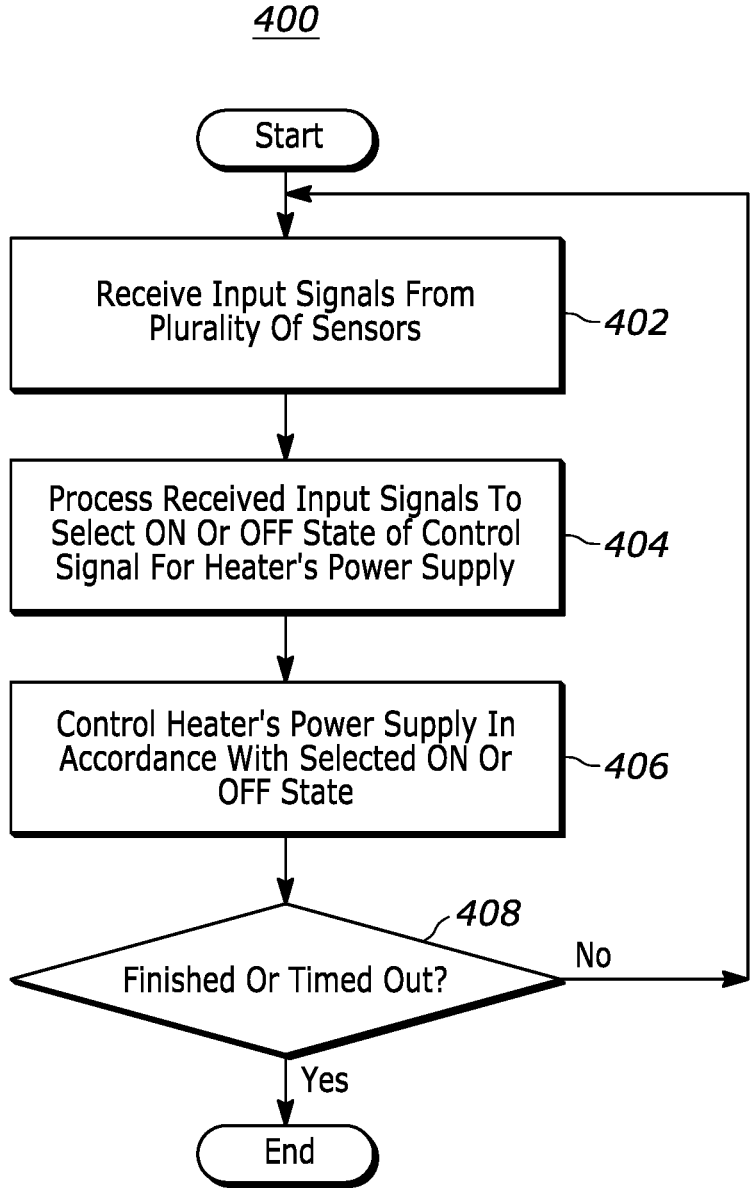
FIG. 4 is a flowchart illustrating an automated control method for the medical system of FIG. 1 according to various examples.

FIG. 4 is a flowchart illustrating an automated control method 400 for the system 10 according to various examples. For illustration purposes and without any implied limitations, the method 400 is described in reference to the example refrigerant delivery sub-system 210 shown in FIG. 3. Based on the provided description, a person of ordinary skill in the pertinent art will be able to implement additional embodiments of the automated control method 400 without any undue experimentation, e.g., embodiments including the reservoir 44. In a representative example, the automated control method 400 is implemented using the electronic controller 48.

The method 400 includes the electronic controller 48 receiving input signals from a plurality of the sensors 50 (in a block 402). In the example sub-system 210 shown in FIG. 3, the plurality of the sensors 50 includes the thermocouples 2681 and 2682, the electronic pressure gauge 270, the weight monitor 348, and the door sensor 350. In some examples, some of the received signals, such as the signals from the weight monitor 348 and the door sensor 350, are binary (e.g., high/low) signals. Some other received signals, such as the signals from the thermocouples 2681 and 2682 and the electronic pressure gauge 270, are analog signals or multibit digital signals. The method 400 also includes the electronic controller 48 digitizing the received analog signals (if any) using an analog-to-digital converter (in block 402).

The method 400 also includes the electronic controller 48 processing the received input signals to decide how to generate the control signal 308 for the power supply 310 (in a block 404). Depending on the processing results of the block 404, the control signal 308 can cause the power supply 310 to turn the blanket-type heater 46 ON or OFF. In various examples, the signal processing performed in the block 404 is implemented using a suitable signal-processing algorithm run by the processor 56 or using a suitably programmed logic circuit (e.g., an FPGA) of the processing circuitry 52.

Several non-limiting examples of the signal processing in the block 404 include one or more of the following logic operations:

(1) If the door sensor 350 indicates that the enclosure door is open, then the control signal 308 is generated to turn OFF the blanket-type heater 46;

(2) If the weight monitor 348 indicates a low (e.g., below a preset weight threshold value) weight load in the receptacle 306, then the control signal 308 is generated to turn OFF the blanket-type heater 46;

(3) If the signal from the thermocouple 2681 indicates a low (e.g., below a first fixed temperature value) temperature, then the control signal 308 is generated to turn ON the blanket-type heater 46. The electronic controller 48 also controls the fan 320 to run at a low rotation speed or be turned OFF;

(4) If the signal from the thermocouple 2681 indicates a high (e.g., above the first fixed temperature value) temperature, then the control signal 308 is generated to turn OFF the blanket-type heater 46. The electronic controller 48 also controls the fan 320 to run at a high rotation speed;

(5) If the signal from the thermocouple 2682 indicates a low (e.g., below a second fixed temperature value) temperature, then the control signal 308 is generated to turn ON the blanket-type heater 46;

(6) If the signal from the thermocouple 2682 indicates a high (e.g., above the second fixed temperature value) temperature, then the control signal 308 is generated to turn OFF the blanket-type heater 46;

(7) If the signal from the electronic pressure gauge 270 indicates a low (e.g., below a fixed pressure value)

pressure, then the control signal 308 is generated to turn ON the blanket-type heater 46; and (8) If the signal from the electronic pressure gauge 270 indicates a high (e.g., above the fixed pressure value) pressure, then the control signal 308 is generated to turn OFF the blanket-type heater 46;

(9) For different temperature readings from the thermocouple 2681, the electronic controller 48 operates to apply suitable control signals to the wireline FM3 to cause the fan 320 to run at a high or low rotation speed or to stop.

In at least some examples, some of the above logic operations are combined using additional logic operations, such as AND, OR, XOR, NAND, NOR, etc., to determine the state of the control signal 308. The various threshold values are selectable and typically depend on the specific parameters and composition of the system 10 and on the type of the refrigerant used therein.

The method 400 also includes the electronic controller 48 generating the control signal 308 (in a block 406). The control signal 308 generated in the block 406 is in accordance with the signal processing performed in the block 404. In response to the control signal 308 generated in the block 406, the power supply 310 operates to turn the blanket-type heater 46 ON or OFF.

The method 400 also includes the electronic controller 48 determining whether or not the medical treatment procedure is finished and/or the heat-delivery period has timed out (in a decision block 408). In some cases, the time-out determination of the decision block 408 is made based on the timer 274 counting the time that is longer than a selected fixed time threshold. In some examples, the fixed time threshold is 30 minutes. In some other cases, the determination of the decision block 408 is made based on the operator input received through the user interface device 62. When the determination is in the affirmative ("Yes" at the decision block 408), the method 400 is terminated. Otherwise ("No" at the decision block 408), the processing of the method 400 is directed back to the block 402.

According to one example disclosed above, e.g., in the summary section and/or in reference to any one or any combination of some or all of FIGS. 1-4, provided is a system for delivering a refrigerant to a medical device, the system comprising: a confined volume to hold pressurized refrigerant therein; an electrical heater arranged to heat the confined volume; and an electronic controller connected to regulate the heater based on input signals received from a plurality of sensors including a temperature sensor in thermal contact with the confined volume and a pressure sensor for measuring a pressure in a refrigerant-delivery line connecting the confined volume and the medical device.

In some examples of the above system, the medical device comprises a cryoablation catheter.

In some examples of any of the above systems, the confined volume comprises a tank having stored therein the pressurized refrigerant; and wherein the temperature sensor comprises a thermocouple in direct thermal contact with an exterior surface of the tank.

In some examples of any of the above systems, the system further comprises a receptacle for the tank; and wherein the plurality of sensors further includes a weight sensor for sensing a weight load in the receptacle.

In some examples of any of the above systems, the confined volume comprises a reservoir for receiving the pressurized refrigerant from a source; and wherein the temperature sensor comprises a first thermocouple in direct thermal contact with an exterior surface of the reservoir.

In some examples of any of the above systems, the confined volume further comprises a tank having stored therein the pressurized refrigerant; and wherein the reservoir is connected, via plumbing, to receive the pressurized refrigerant from the tank and further connected to direct the pressurized refrigerant into the refrigerant-delivery line.

In some examples of any of the above systems, the temperature sensor further comprises a second thermocouple in direct thermal contact with an exterior surface of the tank.

In some examples of any of the above systems, the system further comprises a rollable enclosure; wherein the confined volume is in an interior space of the rollable enclosure; and wherein the plurality of sensors further includes at least one of a thermocouple for sensing air temperature in the interior space and a sensor for sensing status of a door of the rollable enclosure.

In some examples of any of the above systems, the system further comprises a power supply connected to drive an electrical current through the electrical heater; and wherein the electronic controller is configured to generate a control signal for the power supply by processing the input signals, the control signal causing the power supply to regulate the electrical current.

In some examples of any of the above systems, the processing of the input signals includes at least one of: comparing values of at least some of the input signals with one or more threshold values; and using one or more logic operations to decide when to switch the control signal between an ON state and an OFF state, the one or more logic operations being configured for combined processing of two or more of the input signals.

In some examples of any of the above systems, the electronic controller is configured to recognize a plurality of medical devices; and wherein the electronic controller is further configured to use different respective sets of the threshold values for different medical devices of the plurality of medical devices, the different respective sets being stored in a nonvolatile memory of the system.

In some examples of any of the above systems, the refrigerant comprises nitrous oxide.

According to another example disclosed above, e.g., in the summary section and/or in reference to any one or any combination of some or all of FIGS. 1-4, provided is a method for delivering a refrigerant to a medical device, the method comprising: driving an electrical current, with a power supply, through an electrical heater arranged to heat a confined volume holding pressurized refrigerant therein; and regulating the electrical current with an electronic controller connected to the power supply, the regulating being based on input signals received by the electronic controller from a plurality of sensors including a temperature sensor in thermal contact with the confined volume and a pressure sensor for measuring a pressure in a refrigerant-delivery line connecting the confined volume and the medical device.

In some examples of the above method, the regulating comprises: processing the input signals with the electronic controller; and generating, with the electronic controller and based on the processing, a control signal for the power supply, the control signal causing the power supply to regulate the electrical current.

In some examples of any of the above methods, the processing of the input signals includes at least one of: comparing values of at least some of the input signals with one or more threshold values; and using one or more logic operations to decide when to switch the control signal between an ON state and an OFF state, the one or more logic operations being configured for combined processing of two or more of the input signals.

In some examples of any of the above methods, the electronic controller is configured to: recognize a plurality of medical devices; and use different respective sets of the threshold values for different medical devices of the plurality of medical devices.

In some examples of any of the above methods, the plurality of sensors includes one or more of: at least one thermocouple in direct thermal contact with an exterior surface of the confined volume; a weight sensor for sensing a weight load of a receptacle for the confined volume; a thermocouple for sensing air temperature in an enclosure hosting the confined volume therein; and a sensor for sensing status of a door of the enclosure.

In some examples of any of the above methods, the confined volume comprises a reservoir for receiving the pressurized refrigerant from an external pressurized-refrigerant supply line connected thereto.

In some examples of any of the above methods, the confined volume further comprises a tank having stored therein the pressurized refrigerant and a reservoir; and wherein the reservoir is connected, via plumbing, to receive the pressurized refrigerant from the tank and further connected to direct the pressurized refrigerant into the refrigerant-delivery line.

In some examples of any of the above methods, the confined volume comprises a tank having stored therein the pressurized refrigerant.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A system for delivering a refrigerant to a medical device, the system comprising:
   a confined volume to hold pressurized refrigerant therein;
   a first electrical heater arranged to heat the confined volume;

a console connected to the medical device and including an enclosure, wherein the confined volume is within the enclosure;
   a fan configured to circulate air within the enclosure; and
   an electronic controller connected to regulate rotation speed of the fan and the first electrical heater based on input signals received from a plurality of sensors including a first temperature sensor in thermal contact with the confined volume, a second temperature sensor for sensing an air temperature within the enclosure, and a pressure sensor for measuring a pressure in a refrigerant-delivery line connecting the confined volume and the medical device.

2. The system of claim 1, wherein the medical device comprises a cryoablation catheter.

3. The system of claim 1,
   wherein the confined volume comprises a tank having stored therein the pressurized refrigerant; and
   wherein the first temperature sensor comprises a first thermocouple in direct thermal contact with an exterior surface of the tank.

4. The system of claim 3, further comprising a receptacle for the tank; and
   wherein the plurality of sensors further includes a weight sensor for sensing a weight load in the receptacle.

5. The system of claim 3,
   wherein the confined volume further comprises a reservoir connected, via plumbing, to receive the pressurized refrigerant from the tank and further connected to direct the pressurized refrigerant into the refrigerant-delivery line;
   wherein the first temperature sensor comprises a second thermocouple in direct thermal contact with an exterior surface of the reservoir;
   wherein the first electrical heater is configured to heat the tank;
   wherein the second electrical heater is configured to heat the reservoir; and
   wherein the electronic controller is further connected to regulate the second electrical heater based on the input signals received from the plurality of sensors.

6. The system of claim 5,
   wherein the plurality of sensors further includes a sensor for sensing status of a door of the enclosure.

7. The system of claim 1, further comprising a power supply connected to drive an electrical current through the first electrical heater,
   wherein the electronic controller is configured to generate a control signal for the power supply by processing the input signals, the control signal causing the power supply to regulate the electrical current; and
   wherein electronic controller is further configured to use one or more logic operations to regulate the electrical current and the rotation speed of the fan, the one or more logic operations being configured for combined processing of the input signals.

8. The system of claim 5, wherein the electronic controller is configured to:
   compare values of at least some of the input signals with one or more threshold values; and
   use one or more logic operations to regulate the first electrical heater, the second electrical heater, and the rotation speed of the fan, the one or more logic operations being configured for combined processing of the input signals.

9. The system of claim 8, wherein the electronic controller is configured to recognize a plurality of medical devices; and wherein the electronic controller is further configured to use different respective sets of the threshold values for different medical devices of the plurality of medical devices, the different respective sets being stored in a nonvolatile memory of the system.

10. The system of claim 1, wherein the refrigerant comprises nitrous oxide.

11. A method for delivering a refrigerant to a medical device, the method comprising:

driving an electrical current, with a power supply, through an electrical heater arranged to heat a confined volume holding pressurized refrigerant therein, the confined volume being within an enclosure in a console connected to the medical device;

circulating air within the enclosure with a fan; and regulating rotation speed of the fan and the electrical current with an electronic controller connected to the fan and to the power supply, the regulating being based on input signals received by the electronic controller from a plurality of sensors including a first temperature sensor in thermal contact with the confined volume, a second temperature sensor for sensing an air temperature within the enclosure, and a pressure sensor for measuring a pressure in a refrigerant-delivery line connecting the confined volume and the medical device.

12. The method of claim 11, wherein the regulating comprises:

processing the input signals with the electronic controller; and generating, with the electronic controller and based on the processing, a control signal for the power supply, the control signal causing the power supply to regulate the electrical current, wherein the processing comprises using one or more logic operations to regulate the electrical current and the rotation speed of the fan, the one or more logic operations being configured for combined processing of the input signals.

13. The method of claim 12, wherein the processing of the input signals includes:

comparing values of at least some of the input signals with one or more threshold values.

14. The method of claim 13, wherein the electronic controller is configured to:

recognize a plurality of medical devices; and use different respective sets of the threshold values for different medical devices of the plurality of medical devices.

15. The method of claim 11, wherein the plurality of sensors further includes one or more of:

at least one thermocouple in direct thermal contact with an exterior surface of the confined volume;

a weight sensor for sensing a weight load of a receptacle for the confined volume;

a thermocouple for sensing air temperature in the enclosure; and a sensor for sensing status of a door of the enclosure.

16. The method of claim 11, wherein the confined volume comprises a reservoir for receiving the pressurized refrigerant from an external pressurized-refrigerant supply line connected thereto.

17. The method of claim 11, wherein the confined volume comprises a tank having stored therein the pressurized refrigerant and further comprises a reservoir; and wherein the reservoir is connected, via plumbing, to receive the pressurized refrigerant from the tank and further connected to direct the pressurized refrigerant into the refrigerant-delivery line.

18. The method of claim 11, wherein the confined volume comprises a tank having stored therein the pressurized refrigerant.

* * * * *